United States Patent [19]

Atkin et al.

[11] 4,081,372
[45] Mar. 28, 1978

[54] LEAKAGE INDICATOR FOR RECIRCULATING PERITONEAL DIALYSIS SYSTEM

[75] Inventors: Curtis Lyman Atkin; Robert Longfield Stephen, both of Salt Lake City, Utah

[73] Assignee: University of Utah, Salt Lake City, Utah

[21] Appl. No.: 638,729

[22] Filed: Dec. 8, 1975

[51] Int. Cl.² ............................................. B01D 31/00
[52] U.S. Cl. ................................ 210/94; 128/214 R; 210/96 M; 210/321 A
[58] Field of Search ................... 210/22, 321 B, 96 M, 210/94; 252/408; 23/230 B; 128/214 R, 214 B, 214 E

[56] References Cited

U.S. PATENT DOCUMENTS

| | | | |
|---|---|---|---|
| 3,519,572 | 7/1970 | Kita | 252/408 |
| 3,802,562 | 4/1974 | Kozlov et al. | 210/96 |
| 3,873,467 | 3/1975 | Hunt | 23/230 B X |
| 3,900,396 | 8/1975 | Lamadrid | 210/321 B |

OTHER PUBLICATIONS

Shinaberger et al., "Increasing Efficiency—Recirculation Dialysis," from vol. XI, Trans. Amer. Soc. Artif. Int. Organs, 1965 pp. 76–82.

*Primary Examiner*—Frank A. Spear, Jr.

[57] ABSTRACT

Hemoglobin or hemolysate is used as an indicator for leakage detection in the dialysis membrane interface separating the sterile from the nonsterile circuitry in a recirculating peritoneal dialysis system. The indicator is dissolved in the steril dialysis fluid and is retained within the sterile circuit unless leakage occurs in the membrane. Upon rupture or other leakage in the membrane, fluid turbulance and pressure gradient cause crossflow between the sterile and nonsterile circuitry, endangering the patient with infection, peritonitis and endotoxin shock. Such crossflow is detected by the concurrent coloration caused by the mixing of hemoglobin indicator in the nosterile dialysis fluid.

11 Claims, 1 Drawing Figure

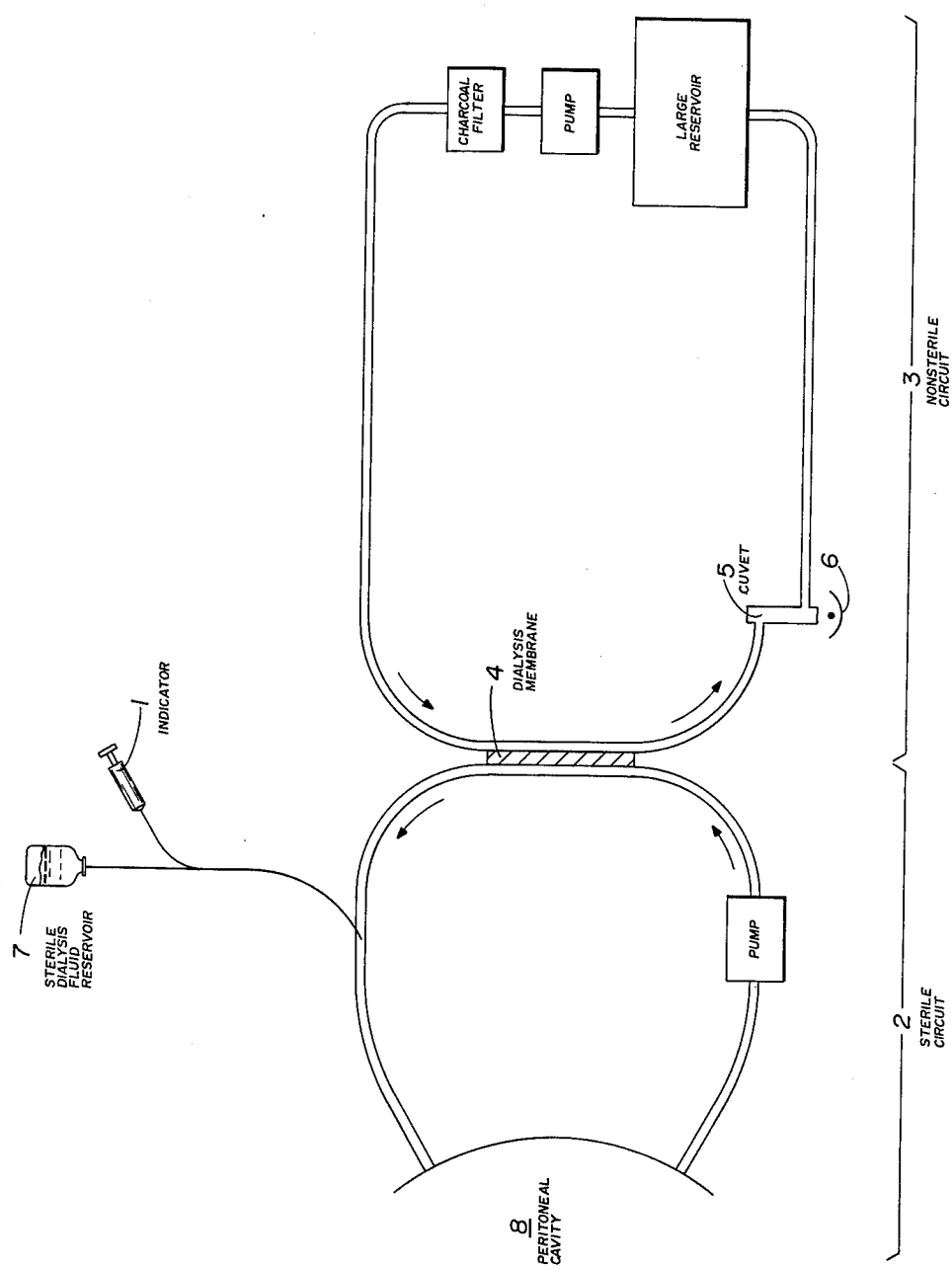

LEAKAGE INDICATOR FOR RECIRCULATING PERITONEAL DIALYSIS SYSTEM

This invention was developed with the support of a research grant from Hematology, National Institute of Arthritis, Metabolism and Digestive Diseases, National Institute of Health, Department of Health, Education and Welfare, United States Government, under Grant No. AM-04489-16.

BACKGROUND OF THE INVENTION

This invention relates to a system and technique for detection of leakage in a peritoneal dialysis membrane, or in leakage or flow in other closed systems where the colorless state of the body fluid being monitored makes visual detection of leakage or flow difficult or impossible.

Current therapy of patients who have suffered kidney failure consists of kidney transplantation or dialysis treatment. Although hemodialysis is at present the best developed and most widely used dialysis technique, it is impractical for patients with clotting or blood-access problems, notably diabetics. Peritoneal dialysis has been demonstrated as a successful alternative treatment for such persons. A severe problem, however, with the recirculating peritoneal dialysis system is the need for rapid detection of the occasional leaks in the dialysis membrane. Statistically, each dialysis treatment has approximately a 5% chance of membrane leakage. Early detection of such leakage is critical because introduction of nonsterile fluid through the membrane into the peritoneal cavity endangers the patient with peritonitis, infection, and endotoxin shock.

Current methods of protecting the patient from such risks are seriously inadequate. Prior to the dialysis, the membrane is subjected to fluid pressure testing to ensure proper working order. Once the treatment is begun, however, membrane failure can be detected only by falling fluid pressure on the sterile side, increasing fluid volume on the nonsterile side, or by appearance of cloudiness in the nonsterile side. The primary weakness of such methods is that only massive leaks can be detected, and the patient may already be endangered before corrective action can begin.

SUMMARY OF THE INVENTION

The present invention utilizes the intense color of hemoglobin to permit immediate detection of membrane leakage from the sterile circuit of the recirculating peritoneal dialysis system. The coloration of the sterile dialysis fluid is accomplished by the addition of hemoglobin or hemolysate indicator. As this colored fluid is pumped through the sterile circuit from the patient to the dialysis membrane and back to the patient in a recirculating manner, the indicator molecules are retained within the sterile system. The nonsterile fluid passing in contact with the other side of the dialysis membrane remains colorless as long as the membrane is functioning properly.

Upon rupture of the membrane during the dialysis process, fluid turbulance causes the hemolysate molecules to pass through the resulting aperture, giving a measureable change of color to the otherwise clear, nonsterile fluid. This color change is detected as the nonsterile fluid passes through an obseravation cell or cuvet within the nonsterile circuit of the dialysis system.

It is an object of the present invention to provide a system and method for detection of leakage or flow in closed parenteral or body fluid systems where the sterile fluid leakage or flow is not easily detectable due to its near colorless state.

It is further an object of this invention to provide a system and method to give immediate warning of rupture or leakage in the dialysis membrane during recirculating peritoneal dialysis treatment.

It is also an object of the present invention to provide a system and method for leakage detection in which the color indicator is of sufficiently large molecular weight that diffusion of the indicator through the dialysis membrane occurs only where an abnormal aperture appears and without interfering with the dialysis process.

It is a further object of the present invention to provide a macromolecular marker with such strong light-absorbing properties, or color, that it be detectable in solution at extreme dilutions by visual or photometric means.

It is another object of the present invention to provide such a system and method in which the indicator is sterile, chemically noninterfering, organically biodegradable, intrinsically nonantigenic, and free of antibodies and of plasma and blood cellular membrane antigens such that no ill effects result from residual indicator remaining within the patient after peritoneal dialysis or other parenteral use.

A further object of the present invention is to provide such a system in which surveillance of dialysis membrane performance may be continued throughout the dialysis administration without interruption, risk or discomfort to the patient.

BRIEF DESCRIPTION OF THE DRAWINGS

The drawing shows a typical peritoneal dialysis system.

DETAILED DESCRIPTION

The above and other objects of the present invention are realized in the following specific illustrative embodiment of a typical recirculating peritoneal dialysis system as shown in the FIGURE. The sterile dialysis fluid is introduced into the sterile circuit 2 from a reservoir of such solution 7. An appropriate amount of indicator is concurrently injected into the sterile circuit from a second reservoir 1 in sufficient quantity to give the sterile fluid adequate color intensity for immediate detection upon leakage. Experimentation has shown that 0.1g/dl (0.1% w/v) hemoglobin is sufficient concentration of indicator to give timely notice of membrane leakage. Larger amounts of indicator may be utilized, however, in view of the harmless nature of the hemolysate.

The colored, sterile fluid is then pumped through the sterile circuit from the peritoneal cavity 8 to the dialysis membrane 4 where the well known dialysis function occurs. If the membrane is functioning properly, the large molecular size of hemolgobin precludes its passage into the nonsterile circuit 3 in which a larger volume of nonsterile dialysis fluid is being circulated on the opposite side of the membrane. After dialysis, the sterile fluid is returned to the peritoneal cavity and the recirculation process continued until completion of the treatment.

If, however, a rupture or leakage in the membrane occurs, fluid turbulance and pressure gradient the hemoglobin to pass into the nonsterile system. The diffusion of even minute quantities of hemolysate indicator into the circulating, nonsterile dialysis fluid results in sufficient coloration of the nonsterile fluid to enable visual or photometric detection at the flow cuvet 5 immediately following the membrane dialyzer within the nonsterile circuit. A standard photometric detector 6 may be utilized for automatic and continuous monitoring of the nonsterile fluid. The attachment of visual and/or audio alarming device provides instantaneous warning of membrane leakage.

Although the patient's own whole blood would serve as an ideal indicator, concurrent anemia usually precludes such blood loss. Consequently, an outside source of indicator is preferable. Although cross-matched donor blood would have the appropriate coloration effect, its repeated use as an indicator is unsatisfactory because of risks of immunological sensitization that might well endanger the success of future kidney transplantation or transfusions. Few kidney-failure patients would willingly foreclose such opportunities for future transplantations or transfusions which might be required for survival.

Utilization, however, of only the hemolysate or hemoglobin from donor blood, instead of whole blood, eliminates the immunological problems discussed above. This distinction arises from the fact that hemoglobin, unlike the blood group antigens, is a molecule essentially equivalent within all persons. Therfore, the risks of antibody reactions accompanying administration of common donor blood are not experienced.

The hemolysate indicator is prepared from donor blood by (1) removal of plasma and buffy coat, (2) saline washing, (3) water hemolysis and (4) centrifugal separation of hemolysate from membranous material and residual cells. These procedures are accomplished in sterile fashion and require only slight modification of standard techniques. Tests for effective removal of ABO and other antigens, and tests for sterility and freedom from endotoxin (pyrogen) are all performed by standard techniques. Inactivation of hepatitis virus is achieved by heat treatment in accordance with current practice for some plasma protein fractions, notably albumin. The indicator may be stabilized for long-term storage by treatment with carbon monoxide and/or by freeze drying.

Hemoglobin is the predominant component of hemolysate indicator prepared as described above. Any minor proteins and metabolites from red cell cytoplasma remaining in the indicator are nontoxic and have no demonstrated allergic effects. Unlike the blood group and histocompatibility antigens, these minor constituents are essentially identical in all people. If desired, however, these extraneous materials may be eliminated by standard techniques for purification of hemoglobin.

We claim:

1. An apparatus for the detection of leakage of a first, substantially colorless sterile solution from a closed system in parenteral administrations, said leakage to occur through an interface means separating said first solution from a second solution wherein the colorless state of the first solution makes visual detection of leakage or flow difficult or impossible, comprising:
   a. a source of hemolysate or other hemoglobin based indicator having strong coloration characteristics upon dilution into larger volumes of colorless solution, and
   b. means for introducing said hemolysate into the first solution in sufficient quantity to develop detectable color intensity upon leakage into said second solution.

2. An apparatus as defined in claim 1, further comprising a means for in-process observation of coloration changes within said second solution.

3. An apparatus as defined in claim 1, further comprising a means for warning of the presence of hemolysate coloration of said second solution.

4. An apparatus as defined in claim 2, further comprising a means for warning of hemolysate coloration of said second solution.

5. In a recirculating peritoneal dialysis system having one or more sterile fluid circuits, one or more nonsterile fluid circuits and appropriate interfaces therebetween, an apparatus for the detection of dialysis membrane leakage, comprising:
   a. a source of hemolysate or other hemoglobin based leakage indicator having strong coloration characteristics, and
   b. means for introducing said hemolysate into a sterile circuit for marking sterile dialysis fluid.

6. An apparatus as defined in claim 5, further comprising a means for observing coloration of circulating nonsterile dialysis fluid immediately following exposure to said dialysis membrane.

7. An apparatus as defined in claim 5, further comprising a means for detecting and/or warning of hemolysate coloration within said nonsterile dialysis circuit.

8. An apparatus as defined in claim 6, wherein the observing means is a cuvet coupled into the nonsterile dialysis circuit to provide a longitudinal view down the length of the cuvet fluid path for increased sensitivity in detection of coloration.

9. An apparatus as defined in claim 6, wherein the observing means is an observation cell coupled into the nonsterile dialysis circuit to enable direct viewing of the circulating nonsterile fluid.

10. An apparatus as defined in claim 6, further comprising a means for warning of the hemolysate coloration within said nonsterile dialysis circuit.

11. An apparatus as defined in claim 7, wherein said detecting means is a photometric monitoring device.

* * * * *